(12) United States Patent
Wong et al.

(10) Patent No.: US 9,877,770 B2
(45) Date of Patent: Jan. 30, 2018

(54) POTENTIAL DRIVEN ELECTROCHEMICAL MODIFICATION OF TISSUE

(71) Applicant: The Regents of the University of California, Oakland, CA (US)

(72) Inventors: Brian Jet-Fei Wong, Irvine, CA (US); Michael G. Hill, Pasadena, CA (US); Dmitry E. Protsenko, Irvine, CA (US); Bryan Hunter, Pasadena, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 547 days.

(21) Appl. No.: 14/280,524

(22) Filed: May 16, 2014

(65) Prior Publication Data

US 2015/0065910 A1    Mar. 5, 2015

Related U.S. Application Data

(60) Provisional application No. 61/824,299, filed on May 16, 2013.

(51) Int. Cl.
| | | |
|---|---|---|
| *A61B 18/12* | (2006.01) | |
| *A61B 18/14* | (2006.01) | |
| *A61B 10/02* | (2006.01) | |
| *A61B 18/00* | (2006.01) | |

(52) U.S. Cl.
CPC ......... *A61B 18/1206* (2013.01); *A61B 10/02* (2013.01); *A61B 18/1477* (2013.01); *A61B 2018/00565* (2013.01); *A61B 2018/1425* (2013.01)

(58) Field of Classification Search
CPC ..... A61B 10/02; A61B 18/12; A61B 18/1206; A61B 18/14; A61B 18/1477; A61B 2018/00565; A61B 2018/1425; A61N 1/0496
USPC ..................................................... 606/33–50
See application file for complete search history.

(56) References Cited

U.S. PATENT DOCUMENTS

| | | |
|---|---|---|
| 5,904,709 A | 5/1999 | Arndt et al. |
| 6,071,280 A | 6/2000 | Edwards et al. |
| 6,557,559 B1 | 5/2003 | Eggers et al. |
| 6,589,235 B2 | 7/2003 | Wong et al. |
| 6,770,070 B1 | 8/2004 | Balbierz |

(Continued)

FOREIGN PATENT DOCUMENTS

WO    WO 2012174161 A1    12/2012

OTHER PUBLICATIONS

Ho, Kevin; Valdes, Sergio H., et al.; Electromechanical Reshaping of Septal Cartilage; Laryngoscope, Nov. 2003; 113:1916-1921.

(Continued)

*Primary Examiner* — Michael Peffley
*Assistant Examiner* — Khadijeh Vahdat
(74) *Attorney, Agent, or Firm* — Shimokaji IP

(57) ABSTRACT

The present invention relates to the use of electrochemistry to control and generate specific user defined chemical reactions in regions that may be defined by electrode placement and geometry. In one embodiment, the present invention provides a method of shape changing cartilage in a subject through potential-driven electrochemical modification of tissue (PDEMT) or use of a potential-driven electromechanical (EMR) device.

34 Claims, 17 Drawing Sheets

(56) References Cited

U.S. PATENT DOCUMENTS

| | | | |
|---|---|---|---|
| 7,416,550 B2 | 8/2008 | Protsenko et al. | |
| 2004/0236320 A1* | 11/2004 | Protsenko | A61B 18/14 606/32 |

OTHER PUBLICATIONS

Protsenko, Dmitriy; Ho, Kevin; Wong, Brian; Stress Relaxation in Porcine Septal Cartilage during Electromechanical Reshaping: Mechanical and Electrical Responses; Annals of Biomedical Engineering, Mar. 2006; 34:455-464.

Manuel, Cyrus T.; Foulad, Allen, et al.; Needle Electrode Based Electromechanical Reshaping of Cartilage; Annals of Biomedical Engineering, Nov. 2010; 38:3389-3397.

Protsenko, Dmitriy; Ho, Kevin; Wong, Brian; Survival of Chondrocytes in Rabbit Septal Cartilage after Electromechanical Reshaping; Annals of Biomedical Engineering, Jan. 2011; 39:66-74.

Manuel, Cyrus; Foulad, Allen, et al.; Electromechanical Reshaping of Costal Cartilage Grafts: A New Surgical Treatment Modality; Laryngoscope, Sep. 2011; 121(9):1839-1842.

Wu, Edward; Protsenko, Dmitriy, et al.; Needle Electrode-based Electromechanical Reshaping of Rabbit Septal Cartilage: A Systematic Evaluation; IEEE Trans Biomed Eng., Aug. 2011.

Lim, Amanda; Protsenko, Dmitriy, et al.; Changes in the Tangent Modulus of Rabbit Septal and Auricular Cartilage Following Electromechanical Reshaping; Journal of Biomechanical Engineering, Sep. 2011; 133:094502.

Oliaei, Sepehr; Manuel, Cyrus; et al.; In Vivo Electromechanical Reshaping of Ear Cartilage in a Rabbit Model: A Minimally Invasive Approach for Otoplasty; JAMA Facial Plastic Surgery, Jan. 2013; 15(1):34-8.

Badran, Karam; Manuel, Cyrus; et al.; Ex Vivo Electromechanical Reshaping of Costal Cartilage in the New Zealand White Rabbit Model; Laryngoscope, Sep. 2013; 121(9):1839-42.

Ho, Kevin; Protsenko, Dmitriy; et al.; Effect of Electrode Composition on Electromechanical Cartilage Reshaping; Proceedings of SPIE, 2003; 4949: 300-306.

Protsenko, Dmitriy; Ho, Kevin; Wong, Brian; Monitoring of Electrical Properties During Cartilage Reshaping; Proceedings of SPIE, 2003; 4949: 307 -310.

Wu, Edward; Khan, Adam; Protsenko, Dmitriy; et al.; Electromechanical Reshaping of Rabbit Septal Cartilage: A Six Needle Geometric Configuration; Proceedings of SPIE, 2009; 7161, 716128.

Lim, Amanda; Protsenko, Dmitriy; et al.; Methods for Evaluating Changes in Cartilage Stiffness Following Electromechanical Reshaping; Head & Neck Oncology, 2010.

Chen, Heather; Yu, Lingfend; et al.; Using Optical Coherence Tomography to Monitor Effects of Electromechanical Reshaping in Septal Cartilage; Head & Neck Oncology, 2010.

Karimi, Koohyar; Protsenko, Dmitriy; et al.; Comparison of Bend Angle Measurements in Fresh Cryopreserved Cartilage Specimens After Electromechanical Reshaping; Head & Neck Oncology, 2010.

Protsenko, Dmitriy; Lim, Amanda; et al.; The Influence of Electric Charge Transferred During Electro-Mechanical Reshaping on Mechanical Behavior of Cartilage; Proceedings of SPIE, 2011; 7901, 790105.

* cited by examiner

- Nasal tip deformity
- Deviated septum
- Protuberant ear
- Stenotic trachea

- Open surgery (cutting, suturing, morselizing tissue)
- Substantial tissue damage (as high as 70% cell mortality)
- High cost (*estimated cost of OR time: $1 per second*)

- Laser Cartilage Reformation
  Wong B.J.F et. Al. JAMA Facial Plastic Surgery, 1999)

Figure 4.

- Electromechanical Reshaping (EMR)

Electromechanical Reshaping of Septal Cartilage

Ki-Hong Kevin Ho; Sergio H. Diaz, Ph.D.; Dimitriy E. Protsenko, Ph.D.; Guillermo Aguilar, Ph.D.; Brian J.F. Wong, M.D., Ph.D.

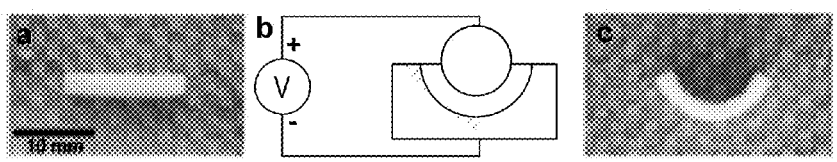

Figure 1: Cartilage EMR, a straight speciman (a) is placed in a reshaping jig (b) attached to a power supply. Current is applied for a period of time. The jig is removed, and a curved specimen is produce (c).

Figure 5.

- Cell viability:

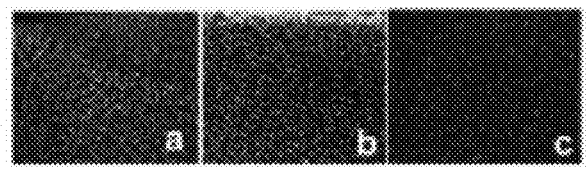

- Dosimetry:

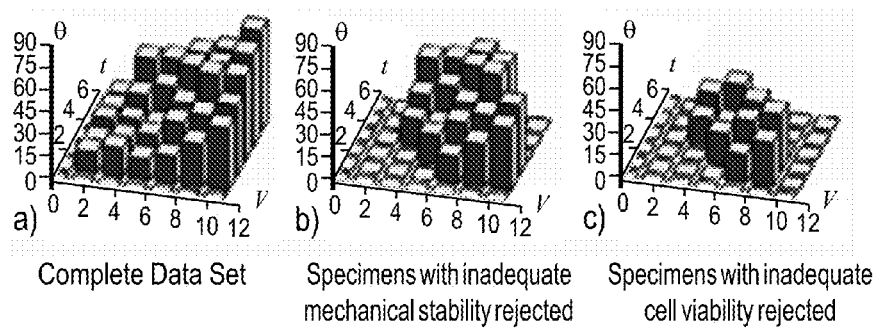

a) Complete Data Set  b) Specimens with inadequate mechanical stability rejected  c) Specimens with inadequate cell viability rejected Carney S.L; Muir H. *Physiological Reviews* 1988, 858.

Figure 9.

- *Dehydration*: hydrogen and dioxygen evolution remove water from the tissue, reducing internal stress during mechanical deformation.

- *Electrophoresis*: mechanically bending specimens changes the internal density of proteoglycans within the cartilage. Application of a voltage across the tissue may lead to migration of charged proteins and a redistribution of ionic bonding.

- *Electrochemistry*: electrochemically generated analytes diffuse into the tissue to reduce internal stress.

Figure 10.

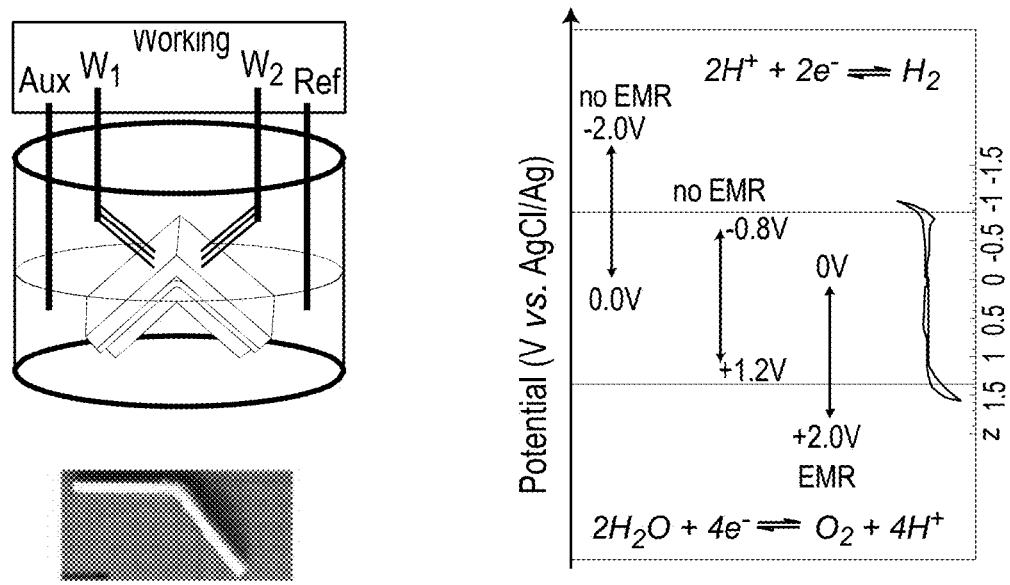

$$C = \frac{q}{4\pi Dr} erfc[\frac{r}{2Dt}]$$

$$2H^+ + 2e^- \rightleftharpoons H_2 \quad (1)$$

$$2H_2O \rightleftharpoons O_2 + 4H^+ + 4e^- \quad (2)$$

$$2\,Cl^- \rightleftharpoons Cl_2 + 2e^- \quad (3)$$

$$Cl_2 + H_2O \rightleftharpoons ClO^- + 2H^+ + Cl^- \quad (4)$$

Figure 25.
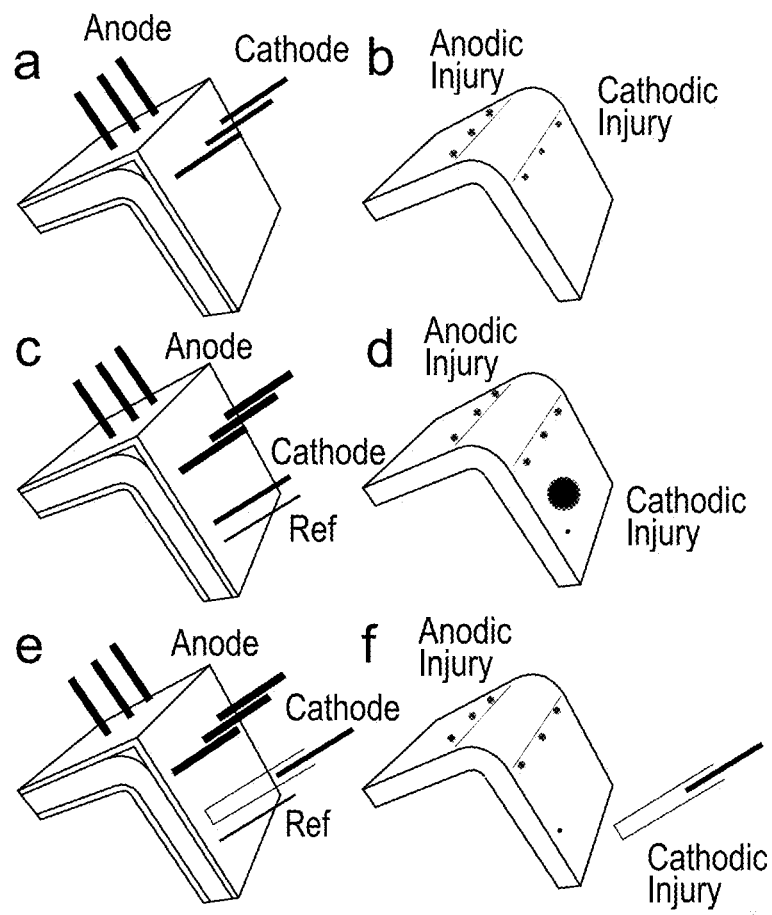
Figure 26.

POTENTIAL DRIVEN ELECTROCHEMICAL MODIFICATION OF TISSUE

CROSS-REFERENCE TO RELATED APPLICATIONS

The present application claims the benefit of priority under 35 U.S.C. §119(e) of provisional application Ser. No. 61/824,299 filed on May 16, 2013, the contents of which are hereby incorporated by reference.

GOVERNMENT RIGHTS

The U.S. Government has a paid-up license in this invention and the right in limited circumstances to require the patent owner to license others on reasonable terms as provided for by the terms of Grant Nos. DR090349 awarded by the Department of Defense Deployment Related Medical Research Program and DE019026 awarded by the National Institutes of Health.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

There are several common cartilage malformations that patients suffer from that require tissue reconstruction and/or shaping cartilage. For example, in the head and neck, a patient could suffer from nasal tip deformity, or a deviated septum, or a protuberant ear, or for example, stenotic trachea. All of the aforementioned conditions could possibly require changing the shape of cartilage tissue of the patient as a form of treatment of the condition. However, changing the shape of tissue such as cartilage is conventionally accomplished using surgical methods that involve sutures, scalpels, incisions, and generally speaking, very invasive methods. Conventional surgical methods of reshaping tissue could require open surgery, resulting in possibly substantial tissue damage, as well as a high financial cost as well. Thus, alternative methods are needed, and there is a need in the art for novel treatments and effective methods of shaping tissue.

BRIEF SUMMARY OF THE INVENTION

Various embodiments herein include a method of modifying a tissue, comprising providing an electrochemical interaction in a tissue, and modifying the tissue by exploiting the electrochemical interaction. In another embodiment, exploiting the electrochemical interaction comprises utilizing an electrochemical potentiostat to apply a specific electrical potential to an array of electrodes. In another embodiment, the electrodes are one or more needle electrodes inserted in the tissue. In another embodiment, exploiting the electrochemical interaction comprises potential-driven electromechanical (EMR) and/or potential-driven electrochemical modification of tissue (PDEMT). In another embodiment, the electrochemical interaction is optimized based on the identification and isolation of one or more discrete electrochemical reactions that cause shape change of the tissue. In another embodiment, the electrochemical interaction is optimized based on specific electrical dosimetry, electrode placement, and/or type of composition. In another embodiment, the tissue comprises a charged polymer hydrogel. In another embodiment, the tissue comprises cartilage. In another embodiment, modifying the tissue is changing the physical shape of the tissue. In another embodiment, modifying the tissue comprises changing physical properties. In another embodiment, changing physical properties includes mechanical behavior-static and dynamic, electrical behavior, optical properties, and/or thermal properties. In another embodiment, modifying the tissue comprises changing biological behavior. In another embodiment, changing biological behavior includes cell injury, cell death, cell proliferation, shape change of the tissue, appearance of the tissue, and/or altering drug delivery properties of the tissue. In another embodiment, modification of the tissue is as part of an overall drug treatment regimen. In another embodiment, the modification of tissue is performed in tandem with one or more defined changes in mechanical state in tissue, temperature of tissue, pressure, compression, and/or atmospheric and ambient conditions. In another embodiment, exploiting the electrochemical interaction in the subject comprises use of a system comprising one or more electrodes and a control system to apply a precise electrical potential.

Other embodiments include a method of treating a disease and/or condition in a subject, comprising defining an electrochemical interaction in a constituent of a tissue and/or organ in a subject, and treating the disease and/or condition by exploiting the electrochemical interaction in the subject. In another embodiment, exploiting the electrochemical interaction results in altering the constituent of living tissue. In another embodiment, the constituent is of one or more of the following: ligament, tendons, cornea, ear drum, temporal mandibular joint, vocal cord, muscle, skin, nerve, brain tissue, and/or tumors. In another embodiment, the constituent is of one or more of the following: cartilage, bone, urine, and/or stool. In another embodiment, treating the disease and/or condition is the treatment of one or more biologic contaminants. In another embodiment, the one or more biologic contaminants include bacteria, fungi, molds, and/or viruses. In another embodiment, exploiting the electrochemical interaction in the subject comprises potential-driven electromechanical (EMR) and/or potential-driven electrochemical modification of tissue (PDEMT). In another embodiment, the subject is a human. In another embodiment, the subject is a rabbit. In another embodiment, exploiting the electrochemical interaction in the subject further comprises placement of working, reference and auxillary electrodes in an effective geometric arrangement. In another embodiment, exploiting the electrochemical interaction in the subject comprises use of a system comprising one or more electrodes and a control system to apply a precise electrical potential.

Other embodiments include a system for exploiting an electrochemical interaction in a subject, comprising one or more electrodes, and a control system to apply a precise electrical potential. In another embodiment, the control system utilizes a potentiostatic control. In another embodiment, the control system utilizes a galvanostatic control. In another embodiment, the control system utilizes operation amplifiers. In another embodiment, the control system further comprises a feedback control. In another embodiment, the feedback control comprises monitoring tissue effect, change in mechanical properties, electrical properties, or optical properties, and total charge transfer. In another embodiment, the feedback control comprises a measure and control of current, potential, charge transfer, pH, concentration of species generated by the system, and/or evolution of gases. In another embodiment, the one or more electrodes comprises a working, reference, and auxillary electrode. In another embodiment, the one or more electrodes have a static placement. In another embodiment, the one or more electrodes are within a flow through cell. In another embodiment, the one or more electrodes have a shape that is needle, flat plate, curved, clamshell, complex, screen, foam, solid-stiff, soft, pliant, moldable, conforming, and/or liquid. In another embodiment, the one or more electrodes are made from platinum, iridium, and/or graphite. In another embodiment, the one or more electrodes are coated with a plurality of oxidation catalysts. In another embodiment, the one or more electrodes comprise sequestered auxillary electrodes in an isolated chamber connected by a salt bridge and/or luggin capillary. In another embodiment, the one or more electrodes are a reference electrode. In another embodiment, the one or more electrodes are composed of base metals and electro-plated. In another embodiment, the applied precise electrical potential is modulated. In another embodiment, the applied precise electrical potential is modulated by pulsed, complex or simple waveform, and/or on and off cycles. In another embodiment, the control system is adapted for use in conjunction with open surgery, endoscopic delivery, percutaneous, transmucosal, in an air environment, in an aqueous environment, image guided therapies to target specific tissues and/or targets, biopsy, and/or tissue sampling. In another embodiment, the control system is used in tandem with one or more of the following: agents that activate a pro-genic drug, user created changes in tissue composition, injectable drugs, agents that produce cross-linking of proteins, agents that alter pH, activate a catalyst for tissue effects, osmotically active agents, saline solutions, buffers, reactive oxygen scavengers, and chemicals that alter electrochemistry of the system. In another embodiment, the system further comprises a plurality of set of electrodes. In another embodiment, the plurality of set of electrodes are used simulatenously or at different times. In another embodiment, the plurality of set of electrodes are used at the same location or spaced apart. In another embodiment, the plurality of set of electrodes are in a multiplexing arrangement of the specific chemical reaction desired. In another embodiment, the system further comprises using an electrochemistry reaction to generate an active polymerization catalyst. In another embodiment, the electrochemistry reaction is described in FIG. 28 herein. In another embodiment, the system further comprises polymerization of polyanaline, polypyrrole, and/or polythiophene.

Various embodiments include a method of shaping cartilage in a patient, comprising: providing a potential-driven electrochemical modification of tissue (PDEMT) and/or potential-driven electromechanical (EMR) device, and using the device to shape cartilage in the patient. In another embodiment, shaping cartilage includes facial structure, lengthening and/or tightening ligaments and tendons, and/or correcting vision in the patient. In another embodiment, cartilage is shaped by water hydrolysis that results in protonation of fixed negative charges. In another embodiment, the method further comprises increasing tissue viability by minimizing pH gradients and/or ROS generation. In another embodiment, the device incorporates bipotentiostat and/or polypotentiostat technology.

Other embodiments include a method of treating a cartilage malformation condition in a patient, comprising providing potential-driven electrochemical modification of tissue (PDEMT) and/or potential-driven electromechanical (EMR) device, and treating the patient by using the device to shape cartilage. In another embodiment, the cartilage malformation condition is a nasal tip deformity, deviated septum, protuberant ear, and/or stenotic trachea. In another embodiment, the device incorporates bipotentiostat and/or polypotentiostat technology. In another embodiment, shaping cartilage includes facial structure, lengthening and/or tightening ligaments and tendons, and/or correcting vision in the patient.

Other embodiments include an apparatus, comprising a potential-driven electrochemical modification of tissue (PDEMT) and/or potential-driven electromechanical (EMR) device adapted for shaping cartilage in a patient. In another embodiment, the device incorporates bipotentiostat and/or polypotentiostat technology.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 4 depicts, in accordance with embodiments herein, some alternative methods of cartilage reshaping.

FIG. 5 depicts, in accordance with embodiments herein, some practical limitations of alternative methods of cartilage reformation.

FIG. 9 depicts, in accordance with embodiments herein, possible EMR mechanisms.

FIG. 10 depicts, in accordance with embodiments herein, controlled-potential EMR.

FIG. 25 depicts, in accordance with embodiments herein, electrodes and jig design for performing EMR of cartilage. v-EMR is illustrated in (a) where both anode and cathode needle electrodes are inserted into tissue creating parallel regions of tissue injury (b). In p-EMR, a potentiostat is used and reference and cathode electrodes are inserted (c), however cathodic tissue injury may be limited to a small region around just one electrode (d) placed distally from the tissue bend. Cathodic injury to the cartilage may be completely eliminated by using a electrolyte gel in a fritted electrode in contact with the cartilage (e), resulting in the cathodic reactions occurring gel which is "sacrificed."

FIG. 26 depicts, in accordance with embodiments herein, electrochemical initiation of Fenton chemistry. In accordance with embodiments herein, the reaction provides an example of one of many chemical reactions that illustrate singlet oxygen generation in this setting. In one embodiment, an iron-metal anode is used and oxidized in the presence of a peroxide. The oxidation produces Fe(II) locally, which reacts with the peroxide for form radicals via the Fenton cycle.

FIG. 27 depicts polymerization of polyanaline. Other examples include electrochemical polymerization of polypyrrole and polythiophene.

DESCRIPTION OF THE INVENTION

Figure 1:
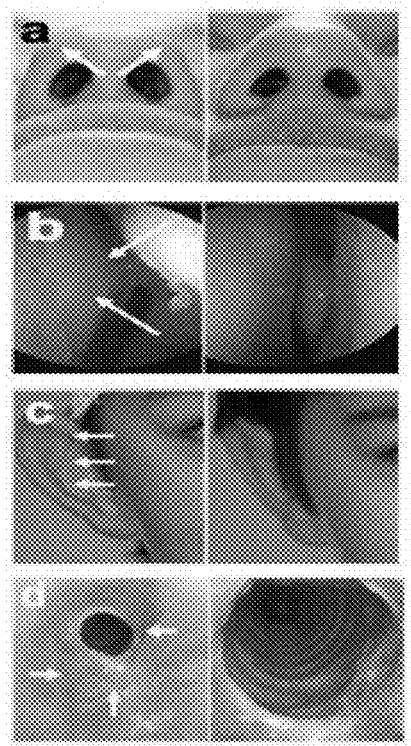
FIG. 1 depicts, in accordance with embodiments herein, common cartilage malformations of the head and neck.
Figure 2:
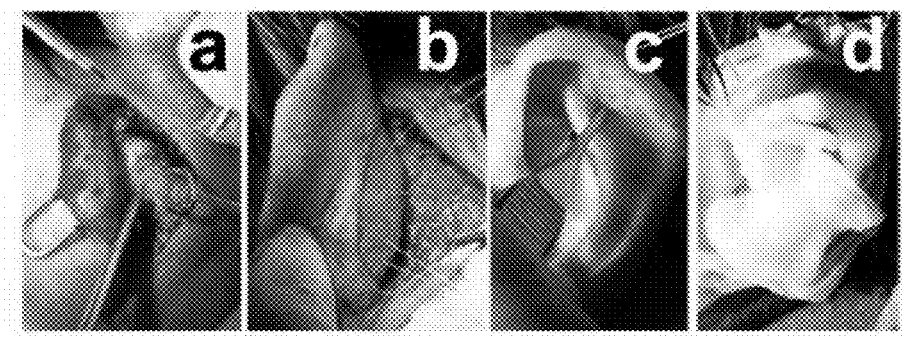
FIG. 2 depicts, in accordance with embodiments herein, some conventional surgical methods for reshaping cartilage.
Figure 3:
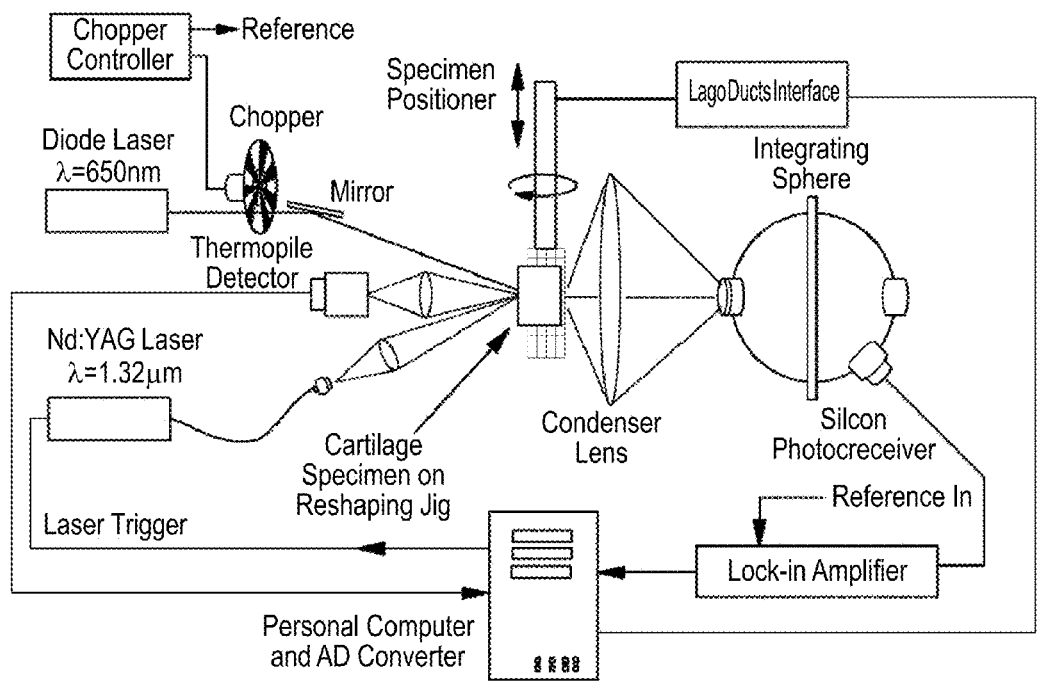
FIG. 3 depicts, in accordance with embodiments herein, some alternative methods of cartilage reformation.
Figure 6:
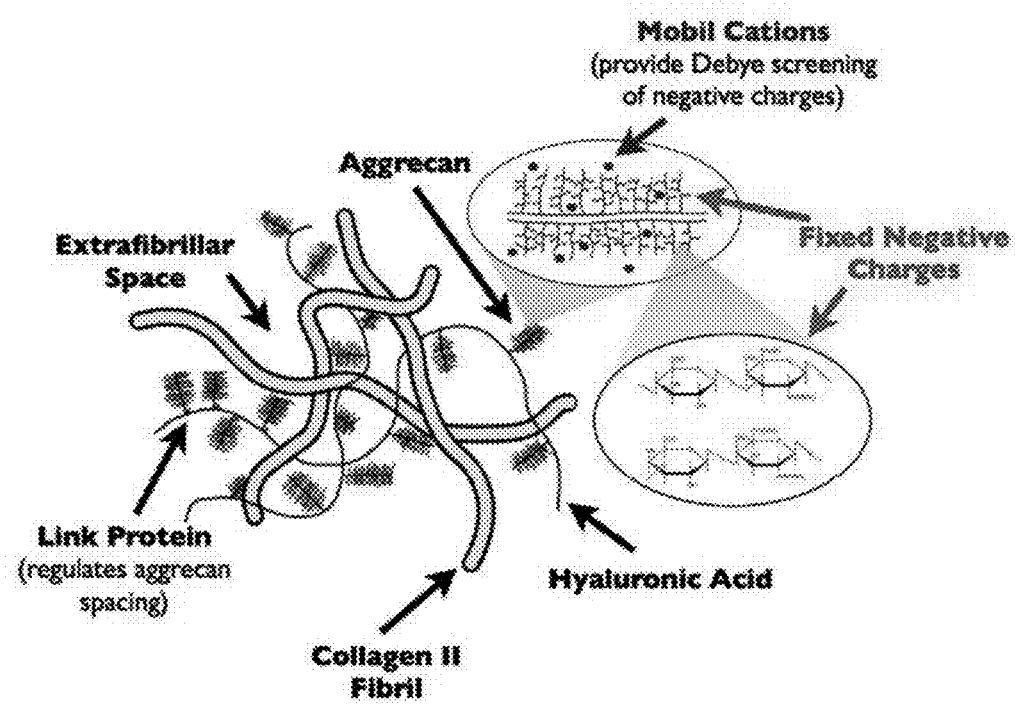
FIG. 6 depicts, in accordance with embodiments herein, a diagram of cartilage.
Figure 7:
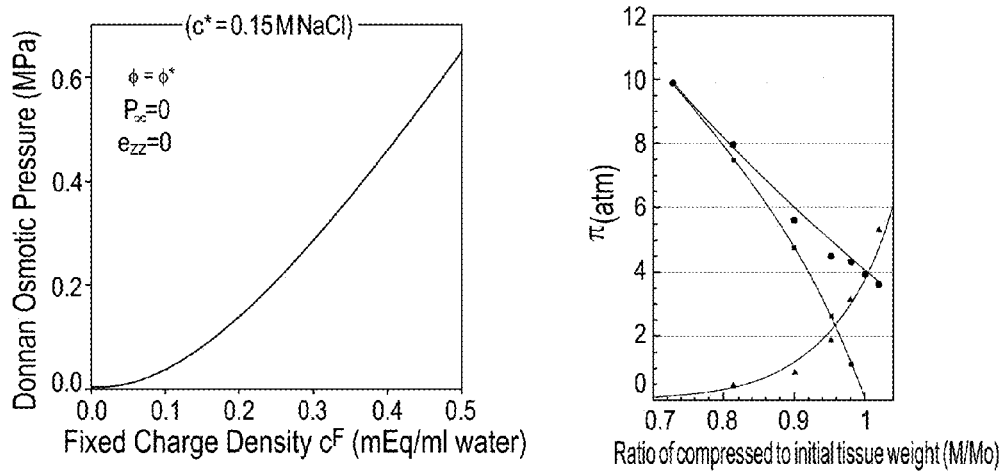
FIG. 7 depicts, in accordance with embodiments herein, charts of osmotic (swelling) pressure due to fixed charge density.
Figure 8:
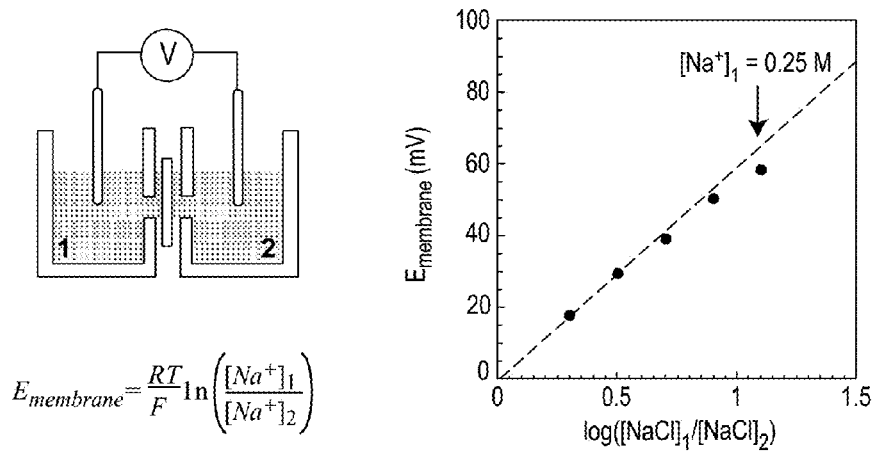
FIG. 8 depicts, in accordance with embodiments herein, donnan exclusion results in cartilage permselectivity.
Figure 11:
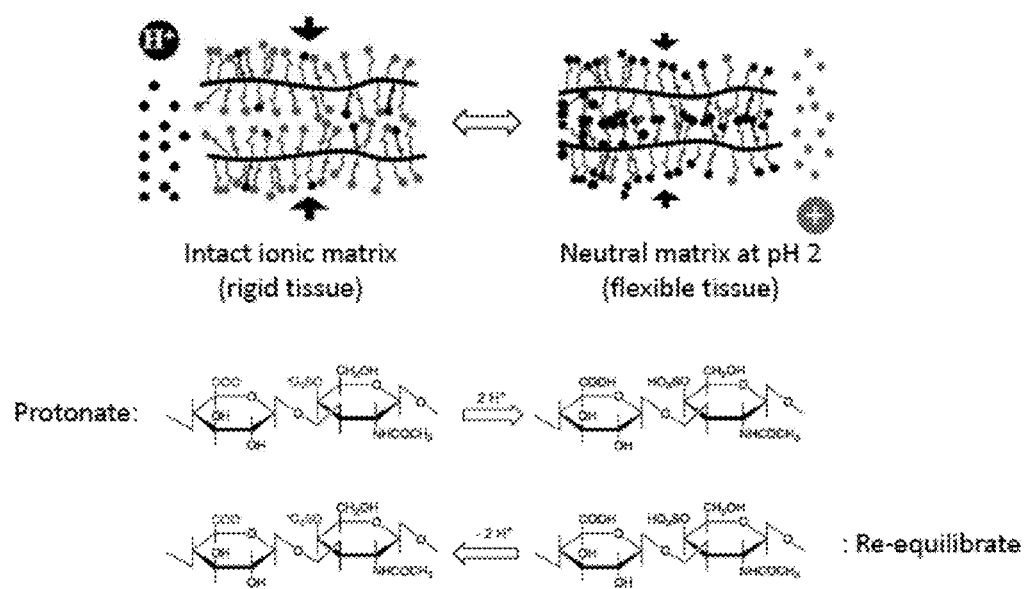
FIG. 11 depicts, in accordance with embodiments herein, a possible mechanism in accordance with embodiments herein, water oxidation and protonation of FCD.
Figure 12:
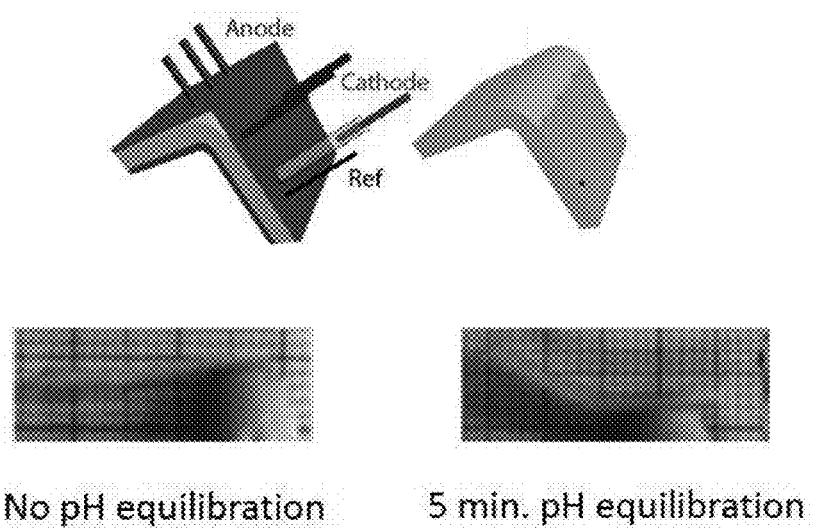
FIG. 12 depicts, in accordance with embodiments herein, electrolysis in PBS buffer at pH 7.4 (1.8 V vs. AgCl/Ag; 3 min; 0.3 C passed).
Figure 13:
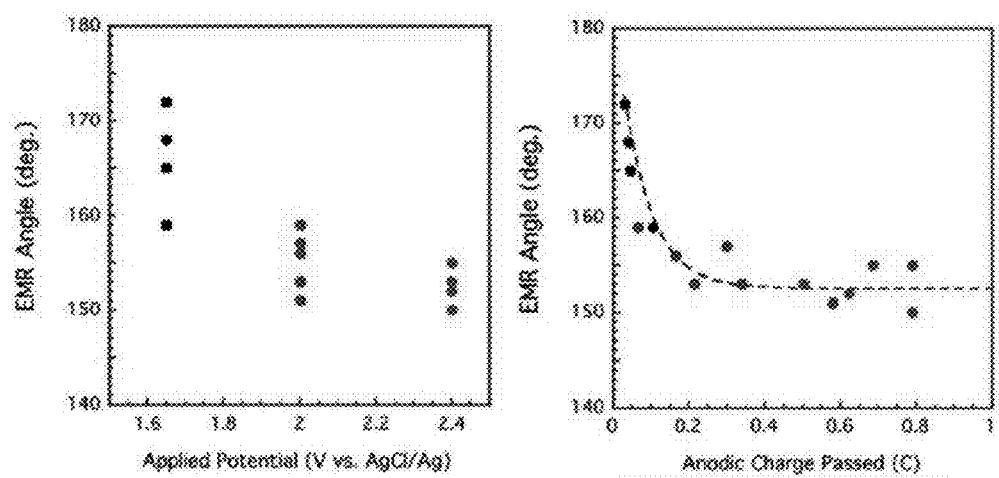
FIG. 13 depicts, in accordance with embodiments herein, shape-change dependence on anodic charge passed.
Figure 14:
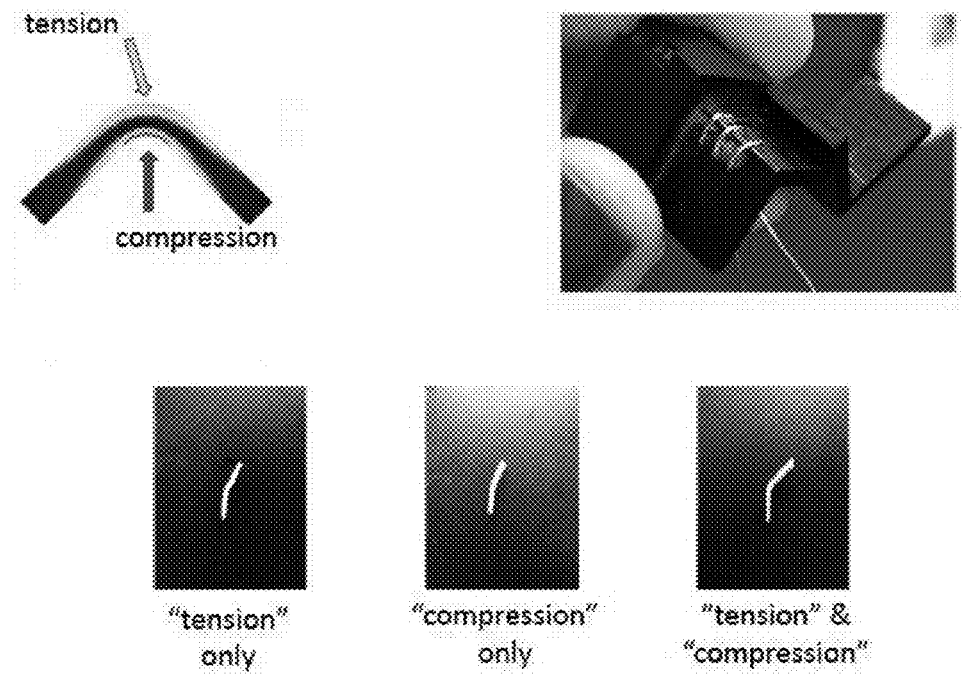
FIG. 14 depicts, in accordance with embodiments herein, role of tension vs. compression stress relief on shape change.
Figure 15:
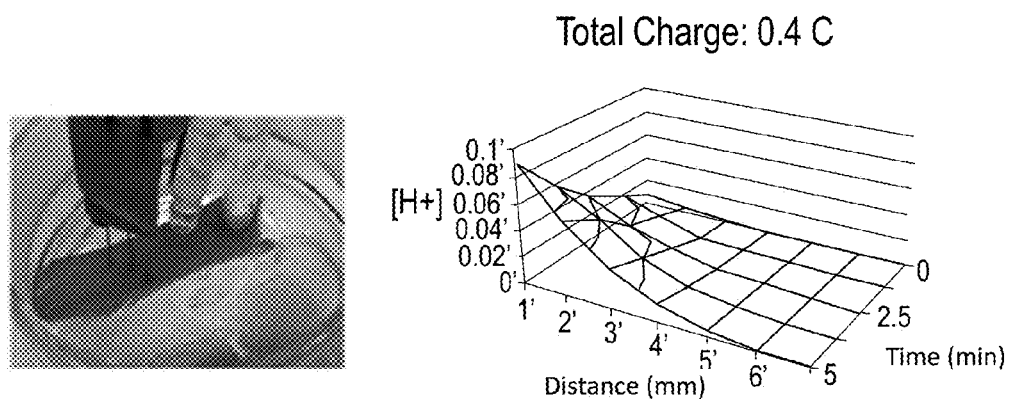
FIG. 15 depicts, in accordance with embodiments herein, empirically derived pH-diffusion landscapes.
Figure 16:
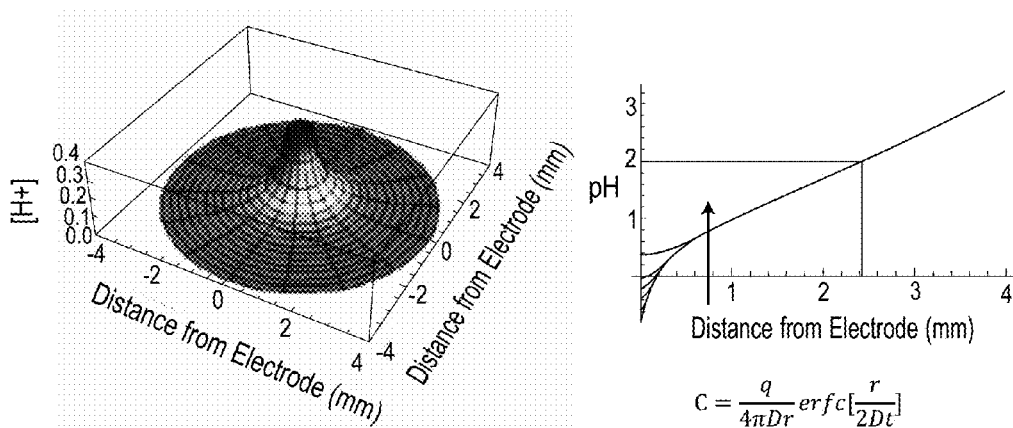
FIG. 16 depicts, in accordance with embodiments herein, possibility of flattening the pH gradient.
Figure 17:
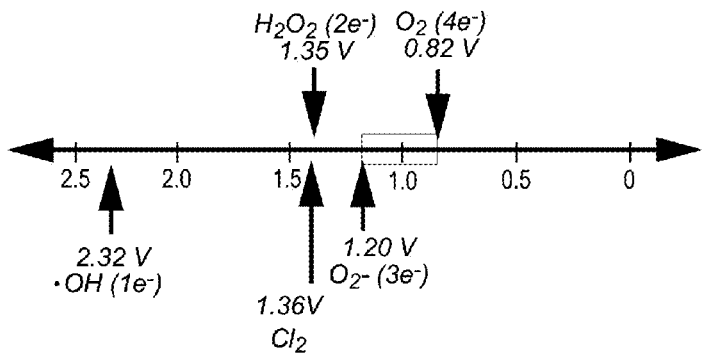
FIG. 17 depicts, in accordance with embodiments herein, possibility of eliminating ROS production.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 4th ed., J. Wiley & Sons (New York, N.Y. 2012); March, Advanced Organic Chemistry Reactions, Mechanisms and Structure 5th ed., J. Wiley & Sons (New York, N.Y. 2001); and Sambrook and Russel, Molecular Cloning: A Laboratory Manual 4th ed., Cold Spring Harbor Laboratory Press (Cold Spring Harbor, N.Y. 2012); provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the abbreviation "PDEMT" refers to potential driven electrochemical modification of tissue.

As used herein, the abbreviation "EMR" means electromechanical reshaping. In one embodiment, EMR provides non-thermal reshaping technique that combines mechanical deformation with the application of low-level DC electric fields.

As disclosed herein, optimization of EMR (or PDEMT) for clinical use requires understanding the role of electrical potential rather than voltage differences, as one can isolate and identify the precise electrochemical reactions that cause events such as shape change or tissue injury. Instead of applying a large voltage difference between two electrodes (v-EMR), potential-driven EMR (p-EMR) utilizes an electrochemical potentiostat to apply a specific electrical potential to an array of electrodes where discrete electrochemical reactions can be isolated. Hence, reactions that favor shape change can be selected over those that cause tissue injury. EMR capitalizes on the innate structure of cartilage as a charged polymer hydrogel, where part of the shape-change process is related to the interplay between charged macromolecular matrix components (proteoglycans), free ions, water, and electrochemical reactions at the interface between tissue and electrode. p-EMR is an elegant, simple, minimally invasive, low-cost technology (e.g., needles, batteries) with the potential to become a clinically useful surgical treatment modality as ubiquitous as the Bovie cautery, surgical stapler, or endoscope in reconstructive surgery.

For example, in accordance with various embodiments herein, cartilage forms the structural framework for the underlying key features of the face and supports the upper airway. The geometry and structure of these frameworks within the ear, nose, larynx, or trachea can become malformed or destroyed as a consequence of trauma, congenital disease, or cancer surgery. EMR related techniques are well suited to alter the shape of both native tissue and autologous grafts obtained from heterotopic sites, and for the ear, nose, or septum, minimally invasive needle-based techniques could be used for in the office under local or regional anesthesia.

As further disclosed herein, the inventors have studied the molecular basis of EMR: most notably, they have established that EMR depends on specific electrochemical reactions at the tissue/solution interface, and examined the role of electrical potential rather than potential difference in the EMR process. With the molecular mechanism(s) of EMR fully characterized, the application of electric fields using p-EMR may be tailored to select the specific reactions that create shape change while minimizing (or even eliminating) the reactions that cause tissue damage and cell morbidity.

In one embodiment, the present invention provides a method of shaping cartilage tissue by using a minimally invasive, needle based approach. As further described herein, in one embodiment, it differs from electrochemical reshaping in that a potentiostat is incorporated to control potential rather than simply applying voltage difference. This can overcome a significant limitation in that specific chemical reactions can be used for therapy and while others are rejected.

In one embodiment, the incorporation of potentiostat technology is used to select specific electrochemical potentials to isolate specific chemical reactions. In another embodiment, the present invention is used to choose between one anodic and/or cathodic half-reaction thereby potentially enhancing/diminishing undesirable outcomes. In another embodiment, the incorporation of a potentiostat is used for multiple tissue electrodes. In another embodiment, the present invention is used to contain and/or localize undesirable half-reactions to a site distal to an organ or tissue of interest (even with the use of a sacrificial electrolyte outside the body, tissue, or organ).

In one embodiment, the technology allows for the use of chemically modified electrodes to further select specific electrochemical reactions to optimize shape and mechanical properties change/minimize tissue damage. The potentiostat can operate in modes where a constant voltage is applied, a constant current is applied, operating in galvanostatic mode, or a pulsed, alternating, or ramped application of voltage or current is used to optimize the concentrations of electrochemically generated species that affect tissue shape change. In another embodiment, the amount of electric charge transferred through each electrode of the bi-/multipotentiostat potential-driven electromechanical (EMR) and/or potential-driven electrochemical modification of tissue (PDEMT) system is monitored and controlled by switching on/off individual electrodes and controlling applied voltage/current.

In other embodiments, the present invention provides a method of shaping cartilage in a patient, comprising providing a potential-driven electromechanical (EMR) and/or potential-driven electrochemical modification of tissue (PDEMT) device, and using the EMR and/or PDEMT device to shape cartilage in the patient. In another embodiment, shaping cartilage includes facial structure, lengthening and/or tightening ligaments and tendons, and/or correcting vision in the patient. In another embodiment, cartilage is shaped by water hydrolysis that results in protonation of fixed negative charges. In another embodiment, the invention further comprises increasing tissue viability by minimizing pH gradients and/or ROS generation. In another embodiment, the device incorporates bipotentiostat and/or polypotentiostat technology.

Other embodiments include a method of treating a cartilage malformation condition in a patient, comprising providing a potential-driven electromechanical (EMR) and/or potential-driven electrochemical modification of tissue (PDEMT) device, and treating the patient by using the PDEMT device to shape cartilage. In another embodiment, the cartilage malformation condition is a nasal tip deformity, deviated septum, protuberant ear, and/or stenotic trachea. In another embodiment, the device incorporates bipotentiostat and/or polypotentiostat technology. In another embodiment, shaping cartilage includes facial structure, lengthening and/or tightening ligaments and tendons, and/or correcting vision in the patient.

Other embodiments include an apparatus, comprising a potential-driven electromechanical (EMR) and/or potential-driven electrochemical modification of tissue (PDEMT) device adapted for shaping cartilage in a patient. In another embodiment, the device incorporates bipotentiostat and/or polypotentiostat technology.

In another embodiment, general surgical or medical device technology may be used to deliver electrical charge or energy to living tissue to create in situ electrochemical reactions. In accordance with various embodiments herein, the reactions can occur with any constituent of living tissue including macromolecules, proteins, etc. and tissue water. This includes cells as well. In another embodiment, the present invention provides use of electrochemistry to control and generate specific user defined chemical reactions in regions defined by electrode placement and geometry. In another embodiment, the invention provides species (agent) selectivity and/or spatial selectivity. As readily apparent to one of skill in the art, a variety of treatments and applications in the human body that depend upon electrochemistry and that require control and optimization may be used in conjunction with various embodiments herein. For example, interactions created can result in the modification of a target tissue for medical therapeutic effects including, change in physical properties (such as mechanical behavior-static and dynamic, electrical behavior, optical properties, or thermal properties), or changes in biologic behavior (such as cell injury, cell death, cancer treatment, cell proliferation, shape change of tissue, appearance of tissue, alter drug delivery properties of tissue). Or, for example, it may be performed in tandem with user imposed or defined changes in mechanical state in tissue (user defined stress-strain), temperature of tissue (heated or cooled), pressure/compression (internal stress), or atmospheric and ambient conditions.

In accordance with various embodiments herein, there are a variety of therapeutic applications possible. For example, therapeutic applications may include all soft tissues and organs including but not limited to ligament and tendons, cornea, ear drum, temporal mandibular joint, vocal cord, muscle, skin, nerve, brain tissue, tumors and cancers. Or, for example, therapeutic applications may also be directed toward cartilage such as may be found in joints, or in airways (ear, nose, throat), or bone, or components that flow such as blood, urine, and stool, allowing electrochemical treatment of flowing constituents. In another embodiment, the present invention provides for eradication, control, and/ or treatment of biologic contaminants including but not limited to bacteria, fungi, molds, and viruses.

As further described herein, in one embodiment the present invention provides for a system that controls the process of current delivery or potential application. In another embodiment, the system has several electrodes including working, reference, and auxiliary. These three electrodes can be placed into tissue in varying geometric arrangements. In another embodiment, there may be more than one of each of these types of electrodes within a therapeutic system. As apparent to one of skill in the art, any number of electrode shapes and materials are readily available and may be used in conjunction with various embodiments herein. For example, the electrode can be static or within a flow through cell, or in the shape of needles, flat plates, complex shapes (such as curves, or clamshell), screens, foams, solid-stiff, soft, pliant, moldable, conforming, or liquid (such as mercury, and other alloys). Or, for example, electrodes could be made of platinum, iridium, graphite, coated with oxidation catalysts, sequestered auxillary electrodes in an isolated chamber connected by a salt bridge or Luggin capillary, reference electrode, or composed of base metals and electro-plated. Similarly, the electrodes may be placed in any number of useful geometric arrangements. For example, in one embodiment, working, reference, and auxiliary electrodes may all be placed within the tissue in either close proximity or at a distance from one another. Or, in another embodiment, an array of working electrodes may be fashioned to cover a large or unique region of interest. In another embodiment, the reference electrode may not interact directly with tissue of interest (e.g. separated by a Luggin capillary or salt bridge). In another embodiment, the auxiliary electrode may not interact directly with tissue of interest (e.g. separated by a Luggin capillary or salt bridge). In another embodiment, the electrical current, charge transfer, and/or potential are modulated. In another embodiment, modulation includes pulsed, complex or simple waveform, and/or on and off cycles. In accordance with various embodiments herein, more than one system or set of electrodes can be used, which can include simultaneously or at different times, or at the same location or spaced apart with variable or constant distances, or multiplexing of the specific chemical reaction desired.

As further disclosed herein, the system that controls the process of current delivery or potential application may also include one or more control system instrumentations. As readily apparent to one of skill in the art, there are a variety of available devices and systems that may be used to provide control instrumentation, as well as any number of elements that may be desired to be monitored and controlled in accordance with various embodiments herein. In one embodiment, the control system instrumentation is a poteniostatic control. In another embodiment, poteniostatic includes biopotentiostats. In another embodiment, the potential is specified by the user. In another embodiment, the control system is a galvanostatic control, where the user can specify certain amounts of current, and potential will be set to establish that current. In another embodiment, simple operation amplifiers can function to accomplish the task of a poteniostatic and/or galvanostatic control. In another embodiment, the system further includes a feedback control. This may include control of tissue effect, where biophysical change can be monitored and information used to control current and/or potential. Or, for example feedback control may include monitored variables that mechanical properties, electrical properties, and optical properties. In another embodiment, total charge transfer is also monitored. In accordance with various embodiments herein, control system instrumentation may be used to measure and/or control one or more of the following: current, potential, charge transfer, pH, concentration of various species generated by the device, and/or the evolution of gases.

In another embodiment, the device is designed for use in one or more of the following: open surgery, endoscopic delivery, percutaneous, trans mucosal, in air and in aqueous environments, combined with image guided therapies to target specific tissues/targets, or perform simultaneous functions such as biopsy and tissue sampling. In accordance with various embodiments herein, the device may be used in tandem with one or more agents that activate a pro-genic drug (e.g. tumorcidal). This may include, for example, reactive oxygen specifies, generate in situ species, or the circumstance where the drug is activated only in vicinity of appropriate/extreme user defined electrical potential. Defined electrical potential may include, for example, creating spatial selectivity based electric field, or isolate deleterious or desired reaction to what is defined by electrode placement geometry. In accordance with various embodiments herein, the device may be used in tandem with user created changes in tissue composition, injectable drugs, agents that produce cross-linking of proteins, agents that alter pH, or activate a catalyst for tissue effects including glue, tumorcidal, or mechanical property change, etc. Similarly, the device may be used in tandem with one or more of the following: osmotically active agents, saline solutions (hyper and hypotonic), buffers, reactive oxygen scavengers, and other chemicals that change or alter electrochemistry of the system.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Overview

In one embodiment, potential driven electrochemical modification of tissue (PDEMT) is a technology that can be used to create discrete electrochemical reactions in tissue. In one embodiment, a potentiostat is employed to select and control the specific electrochemical reactions that occur at an electrode-tissue interface. A potentiostat is the electronic hardware based upon operational amplifiers, and is required to control a three electrode cell and run most electroanalytical experiments. A bipotentiostat and polypotentiostat are potentiostats capable of controlling two working electrodes and more than two working electrodes, respectively. PDEMT implicitly is a new treatment modality that relies upon control of redox chemistry. Redox reactions, or oxidation-reduction reactions, have a number of similarities to acid-base reactions. Like acid-base reactions, redox reactions are a matched set, that is, there cannot be an oxidation reaction without a reduction reaction happening simultaneously. The oxidation alone and the reduction alone are each called a half-reaction, because two half-reactions always occur together to form a whole reaction. When writing half-reactions, the gained or lost electrons are typically included explicitly in order that the half-reaction be balanced with respect to electric charge. A potentiostat allows the separation of the two half-reactions spatially which is important, as in living tissues the major redox reaction that occurs with PDEMT is the electrolysis of water. Complex species may be generated with hydrolysis and PDEMT permits a means to isolate desirable reactions and reduce or eliminate those which are deleterious.

Example 2

Incorporation of Potentiostat Technology

The incorporation of potentiostat technology is important in implementation of this technology as one may a) select specific electrochemical potentials to isolate specific chemical reactions; b) choose between one anodic and/or cathodic half-reaction thereby potentially enhancing/diminishing undesirable outcomes; c) use of multiple tissue electrodes; and d) potential to contain/localize undesirable half-reactions to a site distal to the organ or tissue of interest (even with the use of a sacrificial electrolyte outside the body, tissue, or organ). The technology additionally allows for the use of chemically modified electrodes to further select specific electrochemical reactions to optimize shape and mechanical properties change/minimize tissue damage. The potentiostat can operate in modes where a constant voltage is applied, a constant current is applied (operating in galvanostatic mode), or a pulsed, alternating, or ramped application of voltage or current is used to optimize the concentrations of electrochemically generated species that affect tissue shape change. In addition, amount of electric charge transferred through each electrode of the bi-/multipotentiostat PDEMT system can be monitored and controlled by switching on/off individual electrodes and controlling applied voltage/current.

Example 3

Conclusions

Potential-driven electrochemical modification of tissue (PDEMT) can be used to alter the mechanical structure of living tissues. This would include soft tissue like skin, cartilage, tendon, ligament, cornea, muscle, and others. Using this technology, tissue can be stretched, shortened, bended, curved, strengthened, and weakened. Also, this technology can be used to focally create electrochemical changes locally in tissue as well. Direct application includes the alteration of cartilage to change facial structure, the lengthening or tightening of tendons and ligaments, and the correction of vision. This technology creates electrochemical changes in tissue using a unique means to control the delivery of electrical energy and create specific user-defined electrochemical reactions in localized or diffuse regions in the tissue. The technology allows separation of anodic and cathodic redox chemistry reactions to distinct sites that may be adjacent to one another or separated spatially. This relies upon principles of electrochemistry to alter the complex chemical milieu in living tissue to achieve structural changes and macromolecular alters in the matrix. EMR is an effective and non-invasive method to restructure cartilage tissue, with a dominant mechanism of shape change involving water hydrolysis that results in protonation of fixed negative charges. Additional efforts may be made to minimize pH gradients/ROS generation to further increase tissue viability following EMR.

Example 4 p-EMR

For more than a century, surgeons have envisioned reshaping tissue without the use of scalpels and sutures. Recently, novel laser sources and innovative radiofrequency (RF) devices have brought this vision closer to reality through the development of minimally invasive devices for treating skin and other tissues. The functional and aesthetic defects in the head, neck, and airway that result from cancer surgery, trauma, or congenital malformations require surgical techniques to reshape cartilage in order to restore or recreate damaged or absent structures. Conventional surgical techniques include numerous maneuvers based on carving, morselizing, scoring, or suturing native cartilage tissue. However, the disadvantages of these approaches include donor site morbidity from graft harvest, waste of excess graft tissue, shape memory effects, lack of control over warping (rib cartilage grafts), and the need for anesthesia, scalpels, sutures, and open surgery.

Techniques for reshaping living tissues often rely upon controlled heat generation to denature, remodel, and/or accelerate stress relaxation, exploiting the thermoviscoelasticity common to all collagenous tissues. However, in contrast, electromechanical reshaping (EMR) is a non-thermal reshaping technique that can combine mechanical deformation with the application of low-level DC electric fields. As further disclosed herein, shape change is driven by electrochemical reactions that may occur between surface or needle electrodes placed in contact with or inserted into mechanically deformed specimens.

Figure 18:
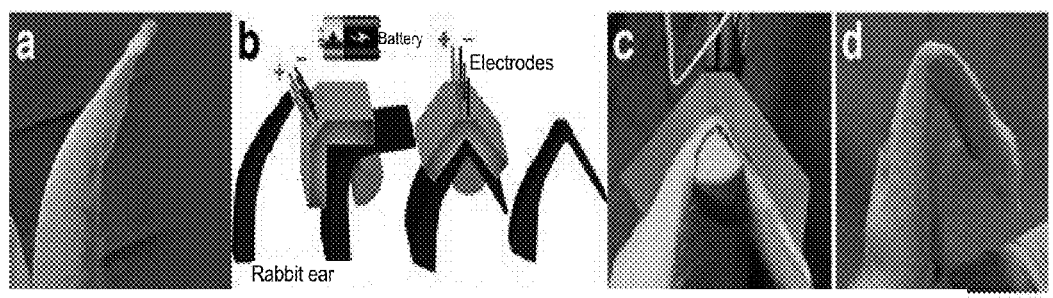
FIG. 18 depicts, in accordance with embodiments herein, electromechanical reshaping of rabbit ear (in vivo) using DC power supply (battery), platinum needles, and acrylic jig.

In a simple embodiment of EMR, namely voltage difference-driven EMR or v-EMR, an intact rabbit ear (FIG. 18a) is held in mechanical deformation by a jig (18b, c). Paired needle electrodes are inserted through the jig and skin into the ear cartilage, and then connected to a DC power supply for 2-3 minutes (18 c). The jigs are then removed, and the ear assumes a new shape, which in this case is a 90° bend (18d). Significantly, the temperature increase during reshaping is negligible (~lo C), which indicates that the mechanism is not due to simple resistive heating. Because the power requirements are extremely small, EMR can be accomplished using disposable batteries as a power source and simple needle electrodes inserted into a mechanically deformed structure such as the ear; these costs are on par with sutures and scalpel blades. Animal studies show that the reshaped ear flexes and behaves mechanically like native tissue.

Optimization of EMR for clinical use requires understanding the role of electrical potential rather than voltage differences, as one can isolate and identify the precise electrochemical reactions that cause events such as shape change or tissue injury. Instead of applying a large voltage difference between two electrodes (v-EMR), potential-driven EMR (p-EMR) utilizes an electrochemical potentiostat to apply a specific electrical potential to an array of electrodes where discrete electrochemical reactions can be isolated. Hence, reactions that favor shape change can be selected over those that cause tissue injury. EMR capitalizes on the innate structure of cartilage as a charged polymer hydrogel, where part of the shape-change process is related to the interplay between charged macromolecular matrix components (proteoglycans), free ions, water, and electrochemical reactions at the interface between tissue and electrode. p-EMR is an elegant, simple, minimally invasive, low-cost technology (e.g., needles, batteries) with the potential to become a clinically useful surgical treatment modality as ubiquitous as the Bovie cautery, surgical stapler, or endoscope in reconstructive surgery.

Cartilage forms the structural framework for the underlying key features of the face and supports the upper airway. The geometry and structure of these frameworks within the ear, nose, larynx, or trachea can become malformed or destroyed as a consequence of trauma, congenital disease, or cancer surgery. To correct these defects, surgery often is needed to alter the shape of these existing cartilaginous structures or the shape of cartilage graft material obtained from heterotopic sites (e.g., rib, ear, septum). Cartilage reshaping is needed to correct four major problems in the head and neck (FIG. 19), namely: structural deformities of the nose a) (currently accomplished by performing rhinoplasty operations; b) nasal airway deformities (e.g., septal deviations, treated with septoplasty) c) prominent/protuberant or malformed ears; and d) acquired subglottic or tracheal stenosis (corrected via many grafting operations). Treatment of each of these conditions requires cartilage reshaping, and the extent of shape change depends on the nature of the defect or deformity. However, the methods used to accomplish these tasks have not changed in decades, and surgeons still rely mainly upon classic surgical techniques (scoring, cutting, suturing). Conventional surgery requires skin or mucosal incisions, almost always general anesthesia, longer operative times and recovery, and additional loss of time from work. EMR related techniques are well suited to alter the shape of both native tissue and autologous grafts obtained from heterotopic sites, and for the ear, nose, or septum, minimally invasive needle-based techniques could be used for in the office under local or regional anesthesia.

Figure 19:
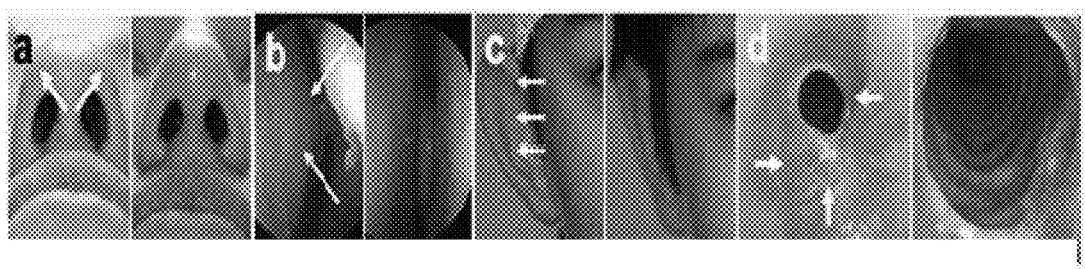
FIG. 19 depicts, in accordance with embodiments herein, cartilage malformations of the face. Specifically, (a) severe boxy nasal tip deformity (pre op left, post op right); (b) deviated septum (left) and after surgery—septoplasty (right); (c) severely protuberant ear (arrows indicate lack of normal fold) and after surgery—otoplasty (right); (d) stenotic tracheal airway (before surgery-left, after-right). Arrows point toward regions of deviation or deformity.

In terms of economic impact, one of the greatest needs for a new, minimally invasive cartilage-reshaping technique is in the management of nasal and septal deformities (FIG. 19 a-b). More than 250,000 septoplasty and 360,000 rhinoplasty operations are performed each year, either to treat nasal airway obstruction or to correct external deformities. In both operations, general anesthesia is normally used, incisions are made, and cartilage is cut, excised, or sutured to alter internal or external nasal shape. Patients miss at least one week of work. The need to develop a simpler office-based method that does not rely upon classic surgical techniques (incisions, sutures, etc.) is clear when the total economic costs of anesthesia, operating room time (estimated to cost an average $1.00/second), nursing and support staff, and surgical fees are tabulated (the total direct costs for conventional nasal surgery is approximately $10,000 per patient; in contrast, the direct costs for most office-based nasal procedures is under $500). EMR, perhaps embodied as a transmucosal/percutaneous needle or probe electrode-based procedure, could potentially be used as a minimally invasive method to reshape cartilage, analogous to that used for laser nasal septum reshaping or auricular cartilage reshaping in the office.

Figure 20:
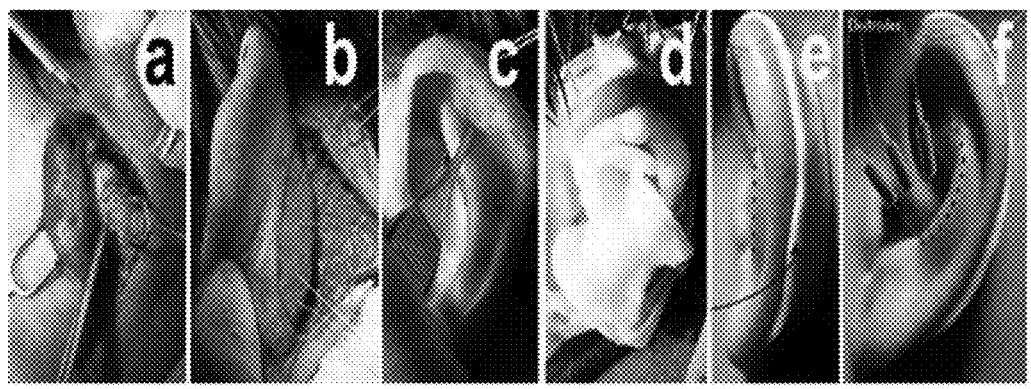
FIG. 20 depicts, in accordance with embodiments herein, techniques to reshape the protuberant human ear. In conventional otoplasty surgery an incision (a) is made in posterior surface of ear. Then strategically placed sutures (b) are used to create the desired curvature and surface contour of the ear. The anterior surface of the ear is shown (c) after curvature creation, and the typical layers of dressing (d) used to maintain curvature for several weeks after surgery. In one example, EMR may be used to reshape the ear is shown in (e) which illustrates the placement of a moulage along the posterior surface of the ear (Arrow) and a series of dots indicating electrode placement (note—anterior surface forming a "clamshell" moulage is eliminated for clarity). Electrodes (f) are inserted along the region where reshaping (stress relaxation) is desired.

In terms of dramatic impact on patients' lives, correcting the spectrum of congenital external ear malformations in young children that include prominent and protuberant ears (FIG. 19c) is also a target application for EMR related techniques and devices. Needle EMR electrodes combined with moulages or molds to hold the ear in mechanical deformation can replace the innumerable otoplasty and auricular reconstruction operations aimed at restoring normal morphology, and reduce the reliance upon surgical skill and technique. Overall, the incidence of external ear deformities in the general population exceeds 5%, and is observed in about 1 in 5,000 live births. The simplest and most common malformation occurs when the antihelical crease of the pinna is missing (FIG. 19 c, left); left uncorrected, the deformity generally leads to vicious ridicule and teasing when the child reaches school age. Correction, while seemingly simple, is a technically demanding process and relies upon expertly placed cartilage-splitting incisions and/or retention sutures to recreate normal anatomy. FIG. 20 herein is a montage of conventional otoplasty (a-d) compared to a hypothetical EMR driven ear reshaping procedure (e-f). In conventional otoplasty surgery, an incision is made along the posterior surface of the ear and skin is dissected and removed to expose the cartilage framework (a). Then precisely placed sutures (b) are used to create the desired curvature and contour. Sutures generally do not resorb and are under significant tension as they must resist the elastic forces generated that resist deformation. Using these techniques the new curvature of the ear is created (c). As considerable tension exists, dressings to maintain cartilage shape (d) are required to be worn by the patient from 1-12 weeks varying widely based upon surgeon preferences. In contrast, EMR could require the ear to be moulded using a two part clamshell-like jig (only one-half shown in (e) for clarity purposes, through which electrodes (f) would be inserted into the cartilage. Once current flows to the electrode, the entire EMR process could take only minutes, after which the moulages would be removed and the ear would retain its new shape. This same general EMR approach could be applied to less complex malformations, such as the "bat" or "shell" ear deformities. Tissue reshaping methods are more than just a nascent technology, as already much more expensive laser ear-reshaping systems are now penetrating the marketplace.

Although they are less common than either nasal or auricular deformities, acquired tracheal malformations may also be treated by EMR (FIG. 19 d). Tracheal and subglottic stenosis in adult and pediatric populations are exceedingly difficult deformities to treat and correct using conventional surgical methods. Tracheal stenosis and related malformations are vexing surgical problems of the upper airway that result from the aggressive development of technology aimed at preserving and prolonging life in both adult and neonatal ICUs, and that develop as a consequence of the extensive use of endotracheal intubation for ventilatory support. Although aggressive ICU care prolongs life, it has led to an increase in the rate of acquired tracheal stenosis, estimated to be between 1 and 8% in the neonatal ICU "graduate" population. Correction of the stenotic tracheal airway generally requires a complex sequence of operations that may involve dilation, laser resection of cartilage, open operations with cartilage graft harvest and placement, or segmental resection. In one embodiment, one possible method to apply EMR would be the development of a needle base system to reshape tissue locally and combine this with short term stent placement—all performed endoscopically by pediatric ENT surgeons.

Presently, surgeons must cut, carve, morselize, or suture cartilage in order to balance the forces generated in the matrix that resist deformation, and these maneuvers require classic open operations, with all the attendant medical risks and increased economic costs of general anesthesia. Recently, a number of thermally mediated procedures have been introduced to replace classic operations in otolaryngology, ophthalmology, plastic surgery, urology, orthopedics, and gastroenterology. However, thermoforming of living tissue exploits the thermoviscoelastic properties inherent within collagen, relying upon heat to produce shape change using laser or RF sources, and has obvious disadvantages in that the desired outcome of shape change must be balanced with the risks of thermal necrosis. In contrast, EMR does not rely upon resistive heat generation, but rather exploits the molecular properties of the cartilage to alter its mechanical state in response to changes in the electrical and chemical milieu that interacts with its charged tissue matrix. EMR is an ultra-low cost, needle-based therapy that can be implemented using only local anesthetics in most applications, and is suitable for office-based procedures. It represents a paradigm shift in that only electrochemical interactions in tissue are exploited to alter the material properties of proteoglycan rich, collagenous tissues, leading to a safe approach to cartilage reshaping. p-EMR, in particular, represents a significant move away from "cut and suture" surgery toward in situ techniques that exploit precisely controlled chemical reactions to restructure tissue at the molecular level. In addition to cartilage tissue, EMR can be used to alter the mechanical behavior of tendon and ligament (tightening) and cornea (reshaping) as well, for example. In addition to the simple needle electrodes and power supplies (e.g., disposable batteries) used for v-EMR, p-EMR may also include an operational amplifier-based circuit for the application of a controlled potential. Thus the p-EMR embodiment of this therapy is low cost and amenable to single-use applications (disposable components); indeed, because the potentiostat can be computer controlled, algorithms for the optimal p-EMR conditions can be pre-programmed into the clinical device to reduce the reliance of good surgical outcome on the individual surgeon's technical skill, much in the model of LASIK cornea reshaping (albeit at a minute fraction of the cost).

Because EMR is, at the molecular level, a consequence of electrode-driven chemical reactions, it builds upon a knowledge base derived from nearly a century of chemistry research in electrochemical processes. That basic research has played key roles in developing industrial technologies ranging from the lithium-ion battery to personal glucose monitors. It is notable that both major professional electrochemical societies—the International Society of Electrochemistry (ISE) and the Electrochemical Society (ECS)—have formal divisions in bioelectrochemistry, yet those divisions focus largely on the electrochemical properties of individual biomolecules (proteins and DNA), or on the development of electrochemical assays for drug metabolites and other molecular markers. The application of modern electroanalytical methods to investigate the effects of electrochemical reactions on macroscopic tissue is virtually unheard of, and offers an innovative model at the interface of basic chemistry, biomedical engineering, and medicine. EMR has the potential to revolutionize the reshaping of cartilage tissue and change the treatment of cartilaginous deformities in the head, neck, and upper airway.

The inventors have studied the molecular basis of EMR: most notably, they have established that EMR depends on specific electrochemical reactions at the tissue/solution interface, and examined the role of electrical potential rather than potential difference in the EMR process. With the molecular mechanism(s) of EMR fully characterized, the application of electric fields using p-EMR may be tailored to select the specific reactions that create shape change while minimizing (or even eliminating) the reactions that cause tissue damage and cell morbidity.

Figure 21:
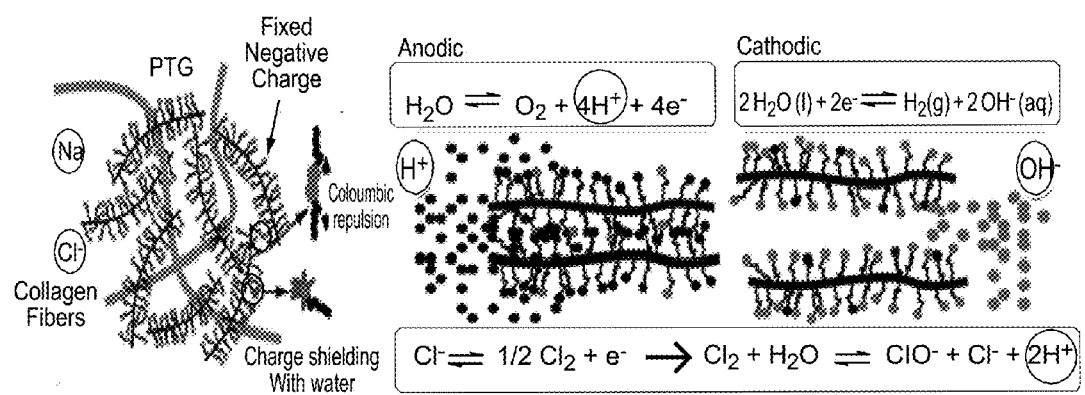
FIG. 21 depicts, in accordance with embodiments herein, electrochemistry and molecular interaction during EMR. Proteoglycans (PTG) are charged under physiologic conditions, and the mechanical properties are dependent upon Coloumbic repulsion. During EMR several reactions occur at the anode, most notably the formation of H+, which can protonate carboxyl and sulfonyl groups. Change in charge of these moieties results in local relaxation and transient softening of the tissue. The generation of OH− in contrast may have a greater effect on tissue injury.

Understanding the underlying molecular mechanism(s) of cartilage EMR is of singular importance to commercializing the reshaping process. Although several possible mechanisms may play a role (e.g., non-Faradaic protein and/or ion migration through the tissue caused by applied voltage gradients), the inventors' work supports that the dominant pathway involves water electrolysis and acidification at the tissue/solution interface. Over the voltage ranges examined in the inventors' previous studies, water and chloride are the main species that undergo redox chemistry. FIG. 21 briefly provides an overview of the electrochemistry and molecular interactions that accompany EMR. Note that chlorine itself does not build up in solution; it is released as a gas or forms hypochlorite instead.

Figure 22:
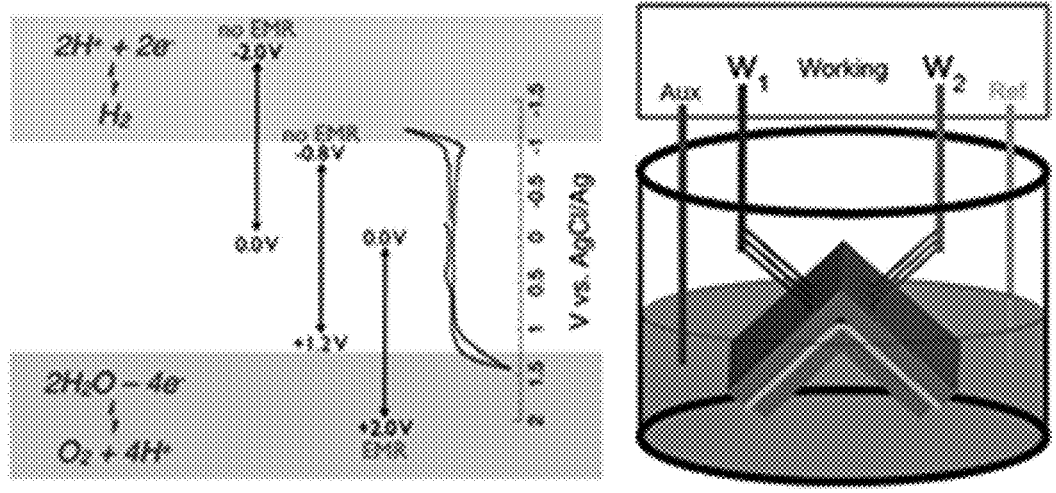
FIG. 22 depicts, in accordance with embodiments herein, summary of EMR shape-change dependence on applied electrochemical potential (diagram, left) using rabbit septal cartilage and platinum-needle apparatus and a bipotentiostat (schematic, inset). In each set of experiments, a constant two-volt potential difference was maintained between the two working electrodes (W1 and W2), while the potentials themselves were poised at successively more positive values vs. a AgCl/Ag reference. Note that in this arrangement, no current flows between W1 and W2. Only when one or both electrodes were held positive of the water oxidation limit did shape change occur. The cyclic voltammogram on the right side of the diagram shows the i-V trace for PBS buffer at a platinum-needle electrode: cathodic current at potentials negative of ~−1 V corresponds to water reduction, while anodic current at potentials positive of ~+1.4 V corresponds to water oxidation.

In order to better control the electrochemical parameters of the p-EMR process, the inventors carried out a series of electrolysis experiments using a bipotentiostat/galvanostat. A four-electrode arrangement (FIG. 22) allows control both of the potential difference between two working electrodes (as in v-EMR), as well as the actual applied potentials (p-EMR) relative to a known reference couple (e.g., AgCl/Ag). Moreover, the bipotentiostat directs current flow between the working electrodes (that are in contact with the cartilage) and a counter electrode that can be positioned far (up to several cm) from the tissue. Thus, in contrast to some previous studies, these experiments do not involve current flow through the tissue sample. This electrode configuration therefore allows one to decouple the effects of current flow on EMR from the effects of applied electrochemical potentials.

Using a platinum-needle EMR apparatus, the inventors performed a series of reshaping experiments on rabbit septal cartilage in which two sets of working electrodes were held at a constant potential difference (2 V) relative to one another, while the midpoint of those potentials was scanned between ±1 V relative to AgCl/Ag, (FIG. 21). Significantly, p-EMR occurred only when the potential of at least one set of working electrodes was held positive of the anodic solvent limit. Hence these results indicate that no potential gradient across the tissue is required for p-EMR: reshaping is just as effective when both working electrodes are held at the same value, as long as that value is positive of the water-oxidation threshold. This is of critical importance as the cathode reactions produce hydroxide [OH—], and base is well known to be more damaging to soft tissues than acid.

Figure 23:
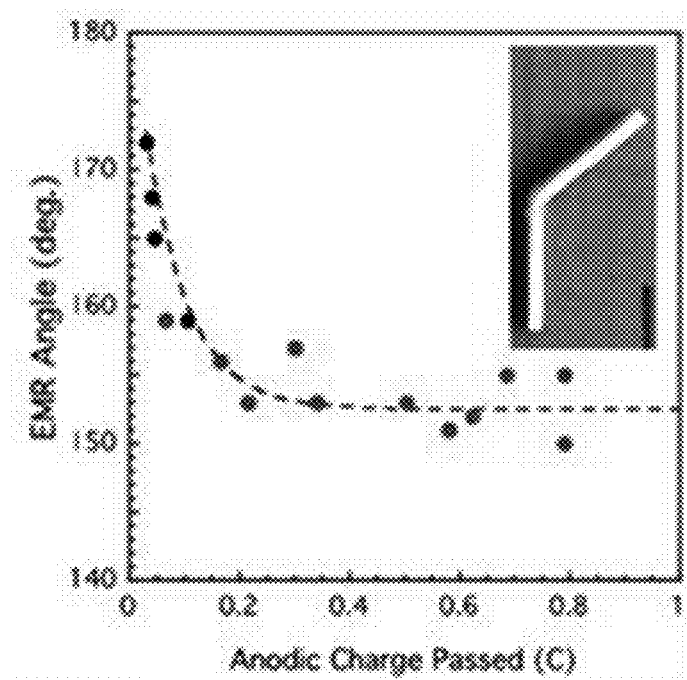
FIG. 23 depicts, in accordance with embodiments herein, p-EMR data for rabbit septal cartilage using Pt-needle apparatus and applied potentials of 1.6 V (black dots), 2.0 V (red dots), and 2.4 V (green dots) vs. AgCl/Ag. The graph shows the bend angle as a function of the anodic charge passed. Inset: image of bent cartilage following 0.8 C passed.

The inventors provide herein compelling evidence that EMR is a result of electrochemical reactions that occur upon oxidation of water/electrolyte at the electrode/tissue interface: (1) no EMR occurs unless at least one electrode in contact with the cartilage is held at a potential positive of the water-oxidation limit; (2) EMR does not require a voltage gradient across the tissue; and (3) the magnitude of EMR correlates directly with total anodic charge transferred (as opposed to electrolysis time, applied potential, voltage gradient, etc. (FIG. 23). This suggests that EMR relies on diffusion into the tissue of key analytes generated during anodic electrolysis. Significantly, water oxidation (as well as chloride oxidation in aqueous media) results in the electrochemical production of H+, whose concentration increases proportionately with the charge passed. Acidification at the anode and subsequent diffusion of protons into the tissue may be the dominant process responsible for the shape change. Protonation of immobilized anions within the proteoglycan matrix disrupts the ionic-bonding network that provides structural integrity to the tissue. This, in turn, relieves the strain imposed by mechanical deformation. Subsequent re-equilibration to physiological pH restores the immobilized negative charges after molecules have locally "shifted" and reestablishes the ionic-bonding matrix, resulting in sustained shape change of the tissue. It is noteworthy that this general mechanism is fully consistent with the observation that EMR persists ex vivo only if samples are pH re-equilibrated in buffer after electrolysis.

In accordance with various embodiments herein, the present invention provides for mapping EMR-induced pH landscapes within cartilage tissue. Under the experimental conditions (applied potential, current density, and electrolysis times) used for p-EMR, homogeneous diffusion through PBS buffer of protons generated at the electrode, result in very low pH's (<~2), with the pH gradient extending 1-2 millimeters into the solution. Modeling proton diffusion through the highly heterogeneous tissue matrix, however, is complicated, as little is known about the dielectric properties of cartilage, which likely change with pH. Mapping the pH gradients by direct measurement of the tissue pH as a function of distance, time, and applied potential is therefore more tractable. Based on the effective pKa's of the acidic forms of chondroitan and keratin sulfate, and the hyaluranan chains of the matrix proteoglycans, it may be estimated that a pH range near 2-3 would be required to protonate the fixed negative charges of the cartilage tissue. From the menu of pH-indicating dyes active in that regime, screening has revealed at least three that show no redox activity at the potentials required for p-EMR: thymol blue, bromophenol blue, and quinaldine red. In experiments using cartilage tissue infused with thymol blue, anodic electrolysis shows the clear evolution of a color change migrating from the Pt-needle anode as the pH gradient moves through the gel. The change in color is readily monitored with a digital camera and compared with the reference color images of stained cartilage samples maintained at known acidity, so pH as a function of distance can be mapped and correlated to anodic charge (and to EMR shape change). Using a series of dyes covering the 0-7 pH range, one can accurately map pH over a wide acidity range to construct an experimentally derived landscape of the tissue pH at any distance and time. This "working curve" may be used to develop protocols for optimizing the electrolysis conditions to give pH gradients that both maximize shape change while potentially minimizing tissue damage.

Because pH staining is independent of the specific p-EMR protocol used, it can provide useful feedback data to alter and refine the p-EMR electrolysis conditions—for example, by applying different electrolysis waveforms (AC vs. DC). Electrochemical pH sensors based on ultra-microelectrodes inserted into the cartilage (using the pH dependence of hydrogen evolution under galvanostatic control as the reporting element) may also be engineered, or using fiber-optic pH probes.

If chloride oxidation limits tissue viability, one might use alternative electrode materials for p-EMR. For example, $IrO_2$ has been identified as one of the best surfaces to carry out the 4e-oxidation of water as it can move the potential threshold from our empirical value of ~1.6 V vs. AgCl/Ag at platinum to near the thermodynamic value, ~0.75 V vs. AgCl/Ag—which is nearly ½ volt negative of the chloride potential. This would effectively eliminate both ROS production and chloride oxidation.

Figure 24:
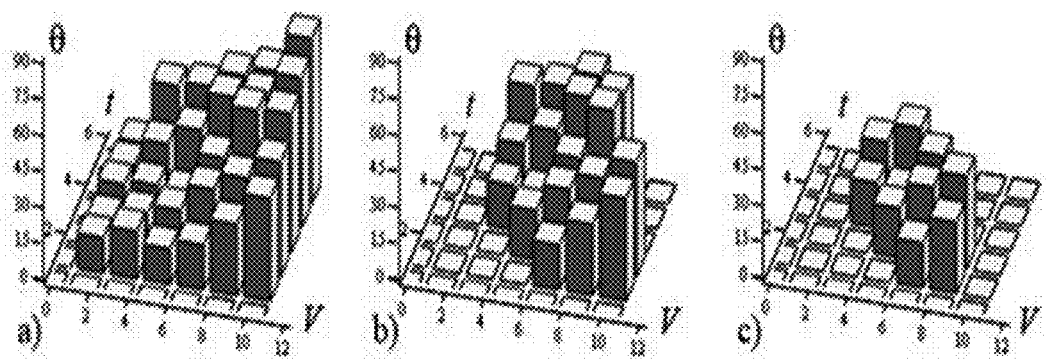
FIG. 24 depicts, in accordance with embodiments herein, identification of dosimetry for EMR as function of V and t. Specifically, (a) complete data set (unique for each electrode configuration) is obtained based upon shape change alone (digital photography). (b) the data set is reduced by rejecting pairs that do not satisfy conditions for adequate mechanical stability. (c) Finally, only specimens with adequate viability (determined using confocal imaging) are candidates for in vivo evaluation. Figures are real data from experiments performed to optimize animal studies in voltage difference driven EMR.
Figure 27:
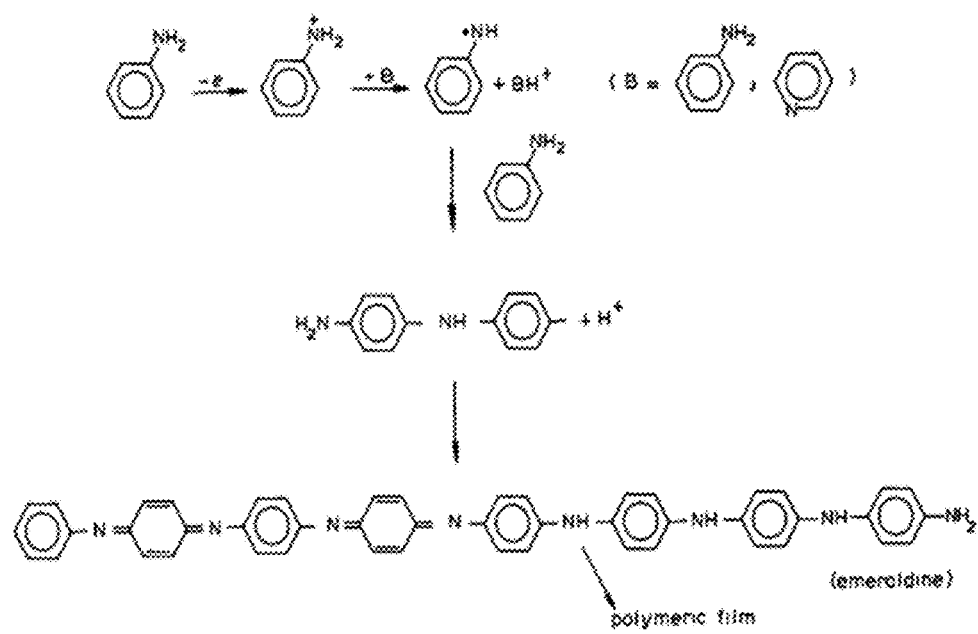
FIG. 27 depicts, in accordance with embodiments herein, an example of electrochemical polymerization. Specifically.
Figure 28:
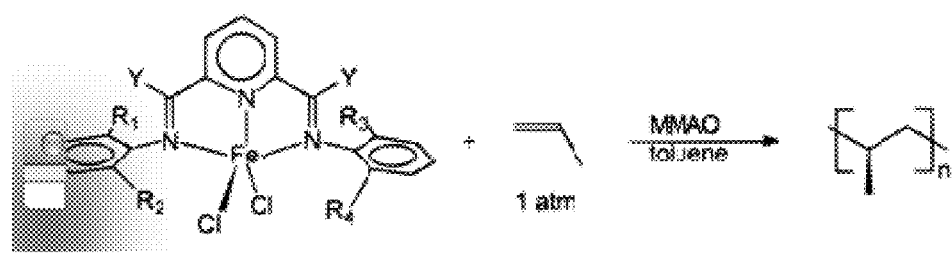
FIG. 28 depicts, in accordance with embodiments herein, an example of using electrochemistry to generate an active polymerization catalyst.

As shape change comes at the expense of cell injury, the optimization may require identification and selection of the appropriate applied potential (V), duration (t), electrode composition, and needle electrode placement. Combinations of these parameters determine resultant shape change, mechanical stability and tissue viability in a cartilage specimen, which are the clinically relevant factors to the reconstructive surgeon (FIG. 24). Analysis may begin with digital photography, and bend angle measured and plotted as a function of potential, electrolysis time, etc. Mechanical stability then measured using flexural mechanical analysis. Viability determined using laser scanning confocal microscopy combined with live-dead assay fluorescent dyes. Electrode placement is constrained by the demand that the shape-change effect occur in regions of increased internal stress produced by the mechanical deformation of the specimen. For a given electrode composition and placement, each V, t combination produces a unique bend angle after EMR (24a). However, not all reshaped specimens will satisfy the criteria for adequate shape change. If mechanical stability is introduced as a second criterion, then the parameter set for V, t, is further reduced (FIG. 24b). Finally, applying tissue viability as a third criterion, the parameter set is even further refined (FIG. 24c). One may also identify a reduced parameter set for p-EMR using shape change and mechanical stability as the outcome measures in ex vivo rabbit nasal septal cartilage tissue for each suitable candidate electrode material. One could further reduce the parameter set by adding viability as the final factor in the selection process. The task at hand is to strike a balance between effective shape change, mechanical stability, and tissue injury.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of modifying a tissue, comprising:
creating stress in the tissue to temporarily maintain a predetermined shape of the tissue;
providing an electrochemical interaction in the tissue comprising an anodic electrode and a cathodic electrode wherein at least the anodic electrode is in contact with the tissue;
acidifying the tissue to a pH range between 0-7 by acidification at the anode and subsequent diffusion of protons to the tissue;
modifying the tissue by diffusion of protons through the tissue; and
re-equilibrating the tissue to physiological pH to sustain the predetermined shape of the tissue.

2. The method of claim 1, wherein providing the electrochemical interaction comprises utilizing an electrochemical potentiostat to apply a specific electrical potential to the electrodes.

3. The method of claim 2, wherein the electrodes are needle electrodes inserted in the tissue.

4. The method of claim 1, wherein providing the electrochemical interaction comprises potential-driven electromechanical (EMR) or potential-driven electrochemical modification of tissue (PDEMT).

5. The method of claim 1, wherein the electrochemical interaction is optimized based on identifying and isolating one or more discrete electrochemical reactions that cause shape change of the tissue.

6. The method of claim 1, wherein the electrochemical interaction is optimized based on specific electrical dosimetry, electrode placement, and/or type of composition.

7. The method of claim 1, wherein the tissue comprises a cartilage tissue.

8. The method of claim 1, wherein modifying the tissue is changing the physical shape of the tissue.

9. The method of claim 1, wherein modifying the tissue comprises changing physical properties of the tissue.

10. The method of claim 9, wherein changing the physical properties of the tissue includes mechanical behavior-static and dynamic, electrical behavior, optical properties, and/or thermal properties.

11. The method of claim 1, wherein modifying the tissue comprises changing biological behavior of the tissue.

12. The method of claim 11, wherein changing the biological behavior of the tissue includes cell injury, cell death, cell proliferation, shape change of the tissue, appearance of the tissue, and/or altering drug delivery properties of the tissue.

13. The method of claim 1, wherein modification of the tissue is a part of an overall drug treatment regimen.

14. The method of claim 1, wherein the modification of tissue is performed in tandem with one or more defined changes in mechanical state in tissue, temperature of tissue, pressure, compression, and/or atmospheric and ambient conditions.

15. The method of claim 1, wherein providing the electrochemical interaction in the tissue comprises use of a system comprising one or more electrodes and a control system to apply a precise electrical potential.

16. A method of treating a disease and/or condition in a subject, comprising:
creating stress in a tissue to temporarily maintain a predetermined shape of the tissue;
providing an electrochemical interaction in a constituent of the tissue and/or organ in a subject wherein the electrochemical interaction comprises at least an anodic electrode and a cathodic electrode, and wherein at least the anodic electrode is in contact with the tissue;
acidifying the tissue to a pH range between 0-7 by acidification at the anode and subsequent diffusion of protons to the tissue; and
treating the disease and/or condition by diffusing protons through the tissue of the subject and subsequent re-equilibration of the tissue to physiological pH.

17. The method of claim 16, wherein providing the electrochemical interaction results in altering the constituent of living tissue.

18. The method of claim 16, wherein the tissue is of one or more of the following: ligament, tendons, cornea, ear drum, temporal mandibular joint, vocal cord, muscle, skin, nerve, brain tissue, and/or tumors.

19. The method of claim 16, wherein the tissue is of one or more of the following: cartilage, bone, urine, and/or stool.

20. The method of claim 16, wherein the disease and/or condition is caused by one or more biologic contaminants.

21. The method of claim 20, wherein the one or more biologic contaminants include bacteria, fungi, molds, and/or viruses.

22. The method of claim 16, wherein providing the electrochemical interaction in the subject comprises potential-driven electromechanical (EMR) or potential-driven electrochemical modification of tissue (PDEMT).

23. The method of claim 16, wherein the subject is a human.

24. The method of claim 16, wherein the subject is a rabbit.

25. The method of claim 16, wherein the at least anodic electrode and cathodic electrode comprise a working electrode, a reference electrode, and an auxiliary electrode, and wherein the working electrode, the reference electrode, and the auxiliary electrode are placed in a geometric arrangement effective for treating the disease.

26. The method of claim 16, wherein providing the electrochemical interaction in the subject comprises use of a system comprising one or more electrodes and a control system to apply a precise electrical potential.

27. A method of shaping cartilage in a patient, comprising:
creating stress in the tissue to temporarily maintain a predetermined shape of the cartilage;
providing a potential-driven electrochemical modification of tissue (PDEMT) or potential-driven electromechanical (EMR) device comprising an anodic electrode and a cathodic electrode wherein at least the anodic electrode is in contact with the cartilage;
acidifying the cartilage to a pH range between 0-7 by acidification at the anode and subsequent diffusion of protons to the cartilage;
using the PDEMT and/or EMR device to shape cartilage in the patient; and
re-equilibrating the cartilage to physiological pH to sustain predetermined shape of the cartilage.

28. The method of claim 27, wherein shaping cartilage comprises shaping a facial structure, lengthening and/or tightening ligaments and tendons, and/or correcting vision in the patient.

29. The method of claim 27, wherein the PDEMT or EMR device is placed in contact with the cartilage in a way to minimize pH gradients and/or Reactive Oxygen Species (ROS) generation.

30. The method of claim 27, wherein the PDEMT or EMR device incorporates bipotentiostat or polypotentiostat technology.

31. A method of treating a cartilage malformation condition in a patient, comprising:
- creating stress in the cartilage to temporarily maintain a predetermined shape of the cartilage;
- providing potential-driven electrochemical modification of tissue (PDEMT) or potential-driven electromechanical (EMR) device comprising an anodic electrode and a cathodic electrode wherein at least the anodic electrode is in contact with the cartilage;
- acidifying the cartilage to a pH range between 0-7 by acidification at the anode and subsequent diffusion of protons to the cartilage;
- treating the patient by using the device to shape cartilage; and
- re-equilibrating the cartilage to physiological pH to sustain predetermined shape of the cartilage.

32. The method of claim 31, wherein the cartilage malformation condition is a nasal tip deformity, deviated septum, protuberant ear, and/or stenotic trachea.

33. The method of claim 31, wherein the PDEMT or EMR device incorporates bipotentiostat or polypotentiostat technology.

34. The method of claim 31, wherein shaping cartilage comprises shaping cartilage in facial structure, lengthening and/or tightening ligaments and tendons, and/or correcting vision in the patient.

* * * * *